M. MATTSON.

Flexible Syringes.

No. 7,971. Reissued Nov. 27, 1877.

WITNESSES.

J. Wm. Garner

Will. H. Krow

INVENTOR.

Morris Mattson per

T. A. Lehmann,

Att'y

N. PETERS, PHOTO-LITHOGRAPHER, WASHINGTON, D. C.

UNITED STATES PATENT OFFICE.

MORRIS MATTSON, OF NEW YORK, N. Y.

IMPROVEMENT IN FLEXIBLE SYRINGES.

Specification forming part of Letters Patent No. 61,750, dated February 5, 1867; Reissue No. 7,971, dated November 27, 1877; application filed November 6, 1877.

*To all whom it may concern:*

Be it known that I, MORRIS MATTSON, of New York, in the county of New York and State of New York, have invented certain new and useful Improvements in Syringes; and I do hereby declare that the following is a full, clear, and exact description thereof, that will enable others skilled in the art to which it appertains to make and use the same, reference being had to the accompanying drawings, and to the letters of reference marked thereon, which form a part of this specification.

My invention relates to improvements in elastic-bulb syringes; and consists in the use of a rigid inflexible inlet-tube, which is capable of being detached from the bulb, and is also separable at a point or place other than at the valve-chamber, so that it can be lengthened or shortened for use or for packing, and also forms a support for the hands and arms in administering an enema, as will be more fully described hereinafter.

Figure 1:
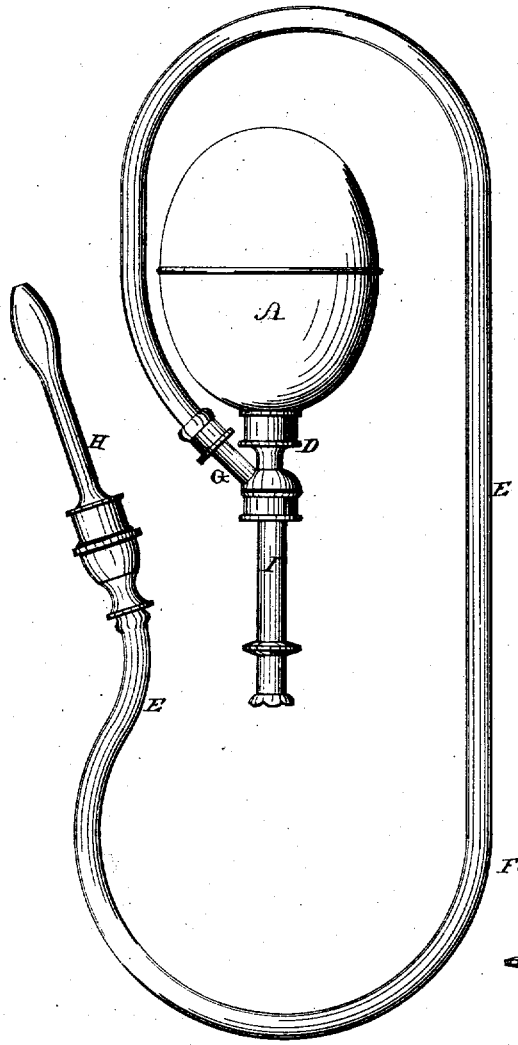
Figure 2:
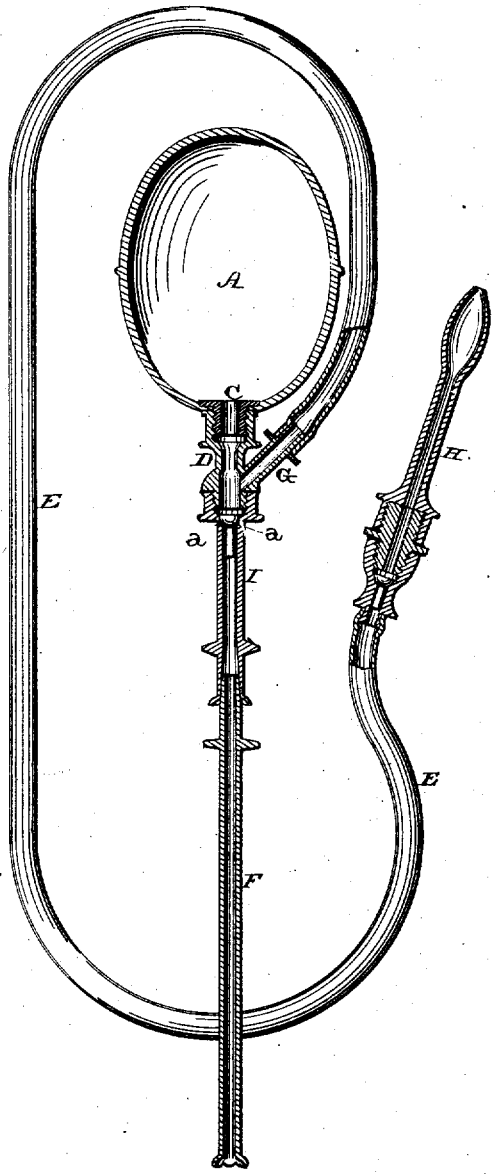
Figure 3:
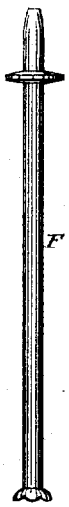

Figure 1 is a side view of my invention. Fig. 2 is a vertical section of the same. Fig. 3 is a detached view of a section of the inlet-tube alone.

A represents the elastic bulb, which is here shown as attached to a screw-coupling, C, as a means of attachment to the rigid sectional inlet pipe or tube, into which the water or other fluid is first drawn up by the bulb or forced by atmospheric pressure before it passes into the flexible outlet-tube. This rigid inlet-tube is divided into sections, to the upper one of which, marked D, the bulb is screwed or otherwise detachably fastened. From the section D extends the pipe G, to which the flexible tube E, having the injection-pipe H fastened to the terminal end, is attached. Upon the lower end of this section D is screwed the rigid inflexible pipe I, which may be made of any length preferred. As here shown, the valve *a* is placed in its top, and the tube is made long enough to reach to the bottom of a shallow vessel; but it is evident that this tube need not be as long as is here shown where it is desired to pack the syringe in a small compass.

When it is desired to make this pipe I longer, so as to adapt it for use in deeper vessels, a sectional pipe, F, is added to it, as shown, so as to increase its length to any desired extent.

By thus making the inlet-tubes of metal or other inflexible substances, instead of the flexible tubes heretofore used, I form a support for the hand and arm during the operation of administering an enema, which is a great convenience; and by making such induction-tube capable of being divided, or separated into sections, it may be lengthened or taken apart, and thus permit the syringe to be packed in a small compass.

It is evident that where the bulb can be readily separated from the section D, or the inlet-tube can be divided, there will be no need of unscrewing the inlet-tube at that point where the valve is located, and thus run the risk of losing the valve.

Having thus described my invention, I claim—

1. In an elastic-bulb syringe, an inlet-tube made in sections for convenience of packing, and made entirely of hard material, so as to form a support for the hand, substantially as described.

2. In an elastic-bulb syringe, the combination of the bulb A, section D, readily detachable therefrom, rigid inlet-tube I, pipe G, and flexible tube E, the inlet-tube being made in sections for convenience of packing, and divisible at another point than at the valve, substantially as shown.

In testimony that I claim the foregoing I have hereunto set my hand this 22d day of October, 1877.

M. MATTSON. [L. S.]

Witnesses:

F. A. LEHMANN,

S. NELSON WHITE.